US010280204B2

(12) United States Patent
Kaplan et al.

(10) Patent No.: US 10,280,204 B2
(45) Date of Patent: May 7, 2019

(54) ELECTROACTIVE BIOPOLYMER OPTICAL AND ELECTRO-OPTICAL DEVICES AND METHOD OF MANUFACTURING THE SAME

(71) Applicant: TUFTS UNIVERSITY, Medford, MA (US)

(72) Inventors: David L. Kaplan, Concord, MA (US); Fiorenzo Omenetto, Lexington, MA (US); Brian Lawrence, Minneapolis, MN (US); Mark Cronin-Golomb, Reading, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 15/046,903

(22) Filed: Feb. 18, 2016

(65) Prior Publication Data

US 2016/0376331 A1 Dec. 29, 2016

Related U.S. Application Data

(63) Continuation of application No. 13/940,168, filed on Jul. 11, 2013, now abandoned, which is a
(Continued)

(51) Int. Cl.
*C07K 14/435* (2006.01)
*D01F 4/02* (2006.01)
(Continued)

(52) U.S. Cl.
CPC ........ *C07K 14/43586* (2013.01); *B29C 39/02* (2013.01); *B29D 11/0074* (2013.01);
(Continued)

(58) Field of Classification Search
CPC .. C07K 14/43586; G02B 1/04; G02B 1/0005; G01N 33/5436; G01N 33/544; D01F 4/02
See application file for complete search history.

(56) References Cited

U.S. PATENT DOCUMENTS 4,676,640 A 6/1987 Briggs
4,977,902 A 12/1990 Sekino et al.
(Continued)

FOREIGN PATENT DOCUMENTS

EP 0245509 A1 11/1987
EP 1025988 A1 8/2000
(Continued)

OTHER PUBLICATIONS

Tetsuo Asakura, Kohei Suita, Tsunenori Kameda, Sergii Afonin and Anne S. Ulrich, Structural role of tyrosine in Bombyx mori silk fibroin, studied by solid-state NMR and molecular mechanics on a model peptide prepared as silk I and II, Magn. Reson. Chem. 2004; 42: 258-266, Copyright _ 2004 JohnWiley & Sons, Ltd.*
(Continued)

*Primary Examiner* — Bijan Ahvazi
(74) *Attorney, Agent, or Firm* — Quarles & Brady LLP

(57) ABSTRACT

A method of manufacturing a biopolymer optical device includes providing a polymer, providing a substrate, casting the polymer on the substrate, and enzymatically polymerizing an organic compound to generate a conducting polymer between the provided polymer and the substrate. The polymer may be a biopolymer such as silk and may be modified using organic compounds such as tyrosines to provide a molecular-level interface between the provided bulk biopolymer of the biopolymer optical device and a substrate or other conducting layer via a tyrosine-enzyme polymerization. The enzymatically polymerizing may include catalyzing the organic compound with peroxidase enzyme reactions. The result is a carbon-carbon conjugated backbone that provides polymeric "wires" for use in polymer and biopolymer optical devices. An all organic biopolymer electroactive material is thereby provided that provides optical functions and features.

15 Claims, 7 Drawing Sheets

Related U.S. Application Data continuation of application No. 12/513,392, filed as application No. PCT/US2007/083639 on Nov. 5, 2007, now Pat. No. 8,574,461.

(60) Provisional application No. 60/856,297, filed on Nov. 3, 2006.

(51) Int. Cl.

| | | |
|---|---|---|
| *B29C 39/02* | (2006.01) | |
| *B29D 11/00* | (2006.01) | |
| *G01N 33/543* | (2006.01) | |
| *G02B 1/04* | (2006.01) | |
| *G02B 6/138* | (2006.01) | |
| *G02B 1/06* | (2006.01) | |
| *G01N 33/544* | (2006.01) | |
| *B82Y 20/00* | (2011.01) | |
| *G02B 6/12* | (2006.01) | |
| *G02B 1/00* | (2006.01) | |
| *G02B 5/18* | (2006.01) | |

(52) U.S. Cl.
CPC .......... *B29D 11/00663* (2013.01); *D01F 4/02* (2013.01); *G01N 33/544* (2013.01); *G01N 33/5436* (2013.01); *G01N 33/54373* (2013.01); *G01N 33/54386* (2013.01); *G02B 1/04* (2013.01); *G02B 1/046* (2013.01); *G02B 1/06* (2013.01); *G02B 6/138* (2013.01); *B82Y 20/00* (2013.01); *D10B 2211/04* (2013.01); *D10B 2401/20* (2013.01); *G01N 2333/43578* (2013.01); *G02B 1/005* (2013.01); *G02B 1/041* (2013.01); *G02B 1/045* (2013.01); *G02B 5/18* (2013.01); *G02B 2006/1213* (2013.01); *G02B 2006/12102* (2013.01); *G02B 2006/12104* (2013.01); *G02B 2006/12107* (2013.01); *G02B 2006/12171* (2013.01)

(56) References Cited

U.S. PATENT DOCUMENTS

| | | |
|---|---|---|
| 4,999,295 A | 3/1991 | Asakura et al. |
| 5,244,799 A | 9/1993 | Anderson |
| 5,252,285 A | 10/1993 | Lock |
| 5,427,096 A | 6/1995 | Bogusiewicz et al. |
| 5,474,915 A | 12/1995 | Dordick et al. |
| 5,512,218 A | 4/1996 | Gresser et al. |
| 5,552,270 A | 9/1996 | Khrapko et al. |
| 6,134,045 A | 10/2000 | Jiang et al. |
| 6,150,491 A | 11/2000 | Akkara |
| 6,284,418 B1 | 9/2001 | Trantolo |
| 6,489,446 B1 | 12/2002 | Rothstein et al. |
| 6,753,064 B1 | 6/2004 | Nakama et al. |
| 6,753,131 B1 | 6/2004 | Rogers et al. |
| 6,924,503 B2 | 8/2005 | Cheng et al. |
| 6,989,897 B2 | 1/2006 | Chan et al. |
| 6,992,325 B2 | 1/2006 | Huang |
| 7,162,127 B2 | 1/2007 | Ohtsu et al. |
| 7,223,609 B2 | 5/2007 | Anvar et al. |
| 7,267,958 B2 | 9/2007 | Dordick et al. |
| 7,427,371 B2 | 9/2008 | Kawanishi et al. |
| 7,476,398 B1 | 1/2009 | Doillon et al. |
| 7,498,802 B2 | 3/2009 | Takahata |
| 7,674,882 B2 | 3/2010 | Kaplan et al. |
| 7,713,778 B2 | 5/2010 | Li et al. |
| 7,828,997 B2 | 11/2010 | Otoshi et al. |
| 8,005,526 B2 | 8/2011 | Martin et al. |
| 8,348,974 B2 | 1/2013 | Asakura |
| 8,529,835 B2 | 9/2013 | Kaplan et al. |
| 8,563,329 B2 | 10/2013 | Yin et al. |
| 8,663,909 B2 | 3/2014 | Gazenko |
| 8,666,471 B2 | 3/2014 | Rogers et al. |
| 8,715,740 B2 | 5/2014 | Wang et al. |
| 8,722,067 B2 | 5/2014 | Wang et al. |
| 8,747,886 B2 | 6/2014 | Amsden et al. |
| 9,171,794 B2 | 10/2015 | Rafferty et al. |
| 9,513,405 B2 | 12/2016 | Kaplan et al. |
| 9,802,374 B2 | 10/2017 | Kaplan et al. |
| 2001/0002417 A1 | 5/2001 | Akkara et al. |
| 2001/0003043 A1 | 6/2001 | Metspalu et al. |
| 2003/0020915 A1 | 1/2003 | Schueller et al. |
| 2003/0162696 A1 | 8/2003 | Mihara |
| 2003/0203366 A1 | 10/2003 | Lim et al. |
| 2003/0214057 A1 | 11/2003 | Huang |
| 2004/0001299 A1 | 1/2004 | van Haaster et al. |
| 2004/0029241 A1 | 2/2004 | Hahn et al. |
| 2004/0081384 A1 | 4/2004 | Datesman et al. |
| 2004/0229349 A1 | 11/2004 | Daridon |
| 2004/0266992 A1 | 12/2004 | Migliaresi et al. |
| 2005/0008675 A1 | 1/2005 | Bhatia et al. |
| 2005/0151966 A1 | 7/2005 | Packirisamy et al. |
| 2005/0164920 A1 | 7/2005 | Doherty et al. |
| 2005/0169962 A1 | 8/2005 | Bhatia et al. |
| 2005/0194365 A1 | 9/2005 | Li |
| 2005/0208469 A1 | 9/2005 | Daunert et al. |
| 2005/0213868 A1 | 9/2005 | Cunningham |
| 2005/0217990 A1 | 10/2005 | Sibbett et al. |
| 2005/0276791 A1 | 12/2005 | Hansford et al. |
| 2006/0024813 A1 | 2/2006 | Warthoe |
| 2006/0042822 A1 | 3/2006 | Azeyanagi et al. |
| 2006/0091571 A1 | 5/2006 | Akutsu et al. |
| 2006/0111517 A1 | 5/2006 | Feucht et al. |
| 2006/0134606 A1 | 6/2006 | Montagu |
| 2006/0141617 A1 | 6/2006 | Desai et al. |
| 2006/0159837 A1 | 7/2006 | Kaplan et al. |
| 2006/0177479 A1 | 8/2006 | Giachelli et al. |
| 2006/0178655 A1 | 8/2006 | Santini et al. |
| 2006/0205927 A1 | 9/2006 | Jin et al. |
| 2006/0226575 A1 | 10/2006 | Maghribi et al. |
| 2006/0236436 A1 | 10/2006 | Li et al. |
| 2007/0007661 A1 | 1/2007 | Burgess et al. |
| 2007/0009968 A1 | 1/2007 | Cunningham et al. |
| 2007/0026064 A1 | 2/2007 | Yoder et al. |
| 2007/0031607 A1 | 2/2007 | Dubson et al. |
| 2007/0042505 A1 | 2/2007 | Israel et al. |
| 2007/0058254 A1 | 3/2007 | Kim |
| 2007/0073130 A1 | 3/2007 | Finch et al. |
| 2007/0113355 A1 | 5/2007 | Knight |
| 2007/0178240 A1 | 8/2007 | Yamazaki et al. |
| 2007/0187862 A1 | 8/2007 | Kaplan et al. |
| 2007/0214520 A1 | 9/2007 | Scheibel et al. |
| 2007/0224677 A1 | 9/2007 | Neumann |
| 2007/0233208 A1 | 10/2007 | Kurtz et al. |
| 2007/0275030 A1 | 11/2007 | Muratoglu et al. |
| 2008/0019925 A1 | 1/2008 | Begleiter |
| 2008/0038236 A1 | 2/2008 | Gimble et al. |
| 2008/0085272 A1 | 4/2008 | Kaplan et al. |
| 2008/0152281 A1 | 6/2008 | Lundquist et al. |
| 2008/0203431 A1 | 8/2008 | Garcia et al. |
| 2008/0239755 A1 | 10/2008 | Parker et al. |
| 2008/0288037 A1 | 11/2008 | Neysmith et al. |
| 2009/0028910 A1 | 1/2009 | DeSimone et al. |
| 2009/0171467 A1 | 7/2009 | Mann et al. |
| 2009/0202614 A1 | 8/2009 | Kaplan et al. |
| 2009/0208555 A1 | 8/2009 | Kuttler et al. |
| 2009/0263430 A1 | 10/2009 | Scheibel et al. |
| 2010/0028451 A1 | 2/2010 | Kaplan et al. |
| 2010/0046902 A1 | 2/2010 | Kaplan et al. |
| 2010/0063404 A1 | 3/2010 | Kaplan et al. |
| 2010/0068740 A1 | 3/2010 | Kaplan et al. |
| 2010/0070068 A1 | 3/2010 | Kaplan et al. |
| 2010/0100975 A1 | 4/2010 | Sutherland et al. |
| 2010/0120116 A1 | 5/2010 | Kaplan et al. |
| 2011/0135697 A1 | 6/2011 | Omenetto et al. |
| 2012/0034291 A1 | 2/2012 | Amsden et al. |
| 2013/0323811 A1 | 12/2013 | Kaplan et al. |

(56) References Cited

U.S. PATENT DOCUMENTS

| | | | |
|---|---|---|---|
| 2014/0205797 A1 | 7/2014 | Kaplan et al. | |
| 2014/0349380 A1 | 11/2014 | Omenetto et al. | |

FOREIGN PATENT DOCUMENTS

| | | | |
|---|---|---|---|
| EP | 1116987 | A2 | 7/2001 |
| EP | 1166987 | A2 | 1/2002 |
| EP | 1209280 | A2 | 5/2002 |
| EP | 1467224 | A1 | 10/2004 |
| JP | 60-142259 | A | 7/1985 |
| JP | 60-155129 | A | 8/1985 |
| JP | H01-135853 | A | 5/1989 |
| JP | 01280242 | A | 11/1989 |
| JP | H02-86799 | A | 3/1990 |
| JP | 11042106 | A | 2/1999 |
| JP | H11-123791 | A | 5/1999 |
| JP | H11-183854 | A | 7/1999 |
| JP | 2000-019119 | A | 1/2000 |
| JP | 2000-096490 | A | 4/2000 |
| JP | 2000-143472 | A | 5/2000 |
| JP | 2000-180969 | A | 6/2000 |
| JP | 2001-147301 | A | 5/2001 |
| JP | 2001280242 | A | 10/2001 |
| JP | 2002-287377 | A | 10/2002 |
| JP | 2003-195001 | A | 7/2003 |
| JP | 2003-322729 | A | 11/2003 |
| JP | 2004162209 | A | 6/2004 |
| JP | 2004-307661 | A | 11/2004 |
| JP | 2005/031724 | A | 2/2005 |
| JP | 2005-530983 | A | 10/2005 |
| JP | 2006-119424 | A | 5/2006 |
| JP | 2006241450 | A | 9/2006 |
| JP | 2011-123791 | A | 6/2011 |
| JP | 05-039368 | B2 | 10/2012 |
| KR | 20060027113 | A | 3/2006 |
| KR | 20070060822 | A | 6/2007 |
| KR | 20080069553 | A | 7/2008 |
| WO | WO-1993/015244 | A1 | 8/1993 |
| WO | WO-96/05510 | A2 | 2/1996 |
| WO | WO-2000/31752 | A2 | 6/2000 |
| WO | WO-01/10464 | A1 | 2/2001 |
| WO | WO-2001/85637 | A2 | 11/2001 |
| WO | WO-03/038033 | A2 | 5/2003 |
| WO | WO-04/000915 | A2 | 12/2003 |
| WO | WO 2004/000915 | A2 * | 12/2003 |
| WO | WO-2004/071949 | A2 | 8/2004 |
| WO | WO-2004/092250 | A1 | 10/2004 |
| WO | WO-05/012606 | A2 | 2/2005 |
| WO | WO-2005/019503 | A2 | 3/2005 |
| WO | WO-05/031724 | A1 | 4/2005 |
| WO | WO-2005/103670 | A1 | 11/2005 |
| WO | WO-05/123114 | A2 | 12/2005 |
| WO | WO-2006/020507 | A1 | 2/2006 |
| WO | WO-2008/004356 | A1 | 1/2008 |
| WO | WO-2008/118211 | A2 | 10/2008 |
| WO | WO-2008/127402 | A2 | 10/2008 |
| WO | WO-2008/127403 | A2 | 10/2008 |
| WO | WO-2008/127404 | A2 | 10/2008 |
| WO | WO-2008/127405 | A2 | 10/2008 |
| WO | WO-2008/140562 | A2 | 11/2008 |
| WO | WO-2009/061823 | A1 | 5/2009 |
| WO | WO-2010/042798 | A2 | 4/2010 |
| WO | WO-2010059963 | A2 | 5/2010 |
| WO | WO-2010/126640 | A2 | 11/2010 |

OTHER PUBLICATIONS

Anderson, J. et al., Bioactive Silk-Like Protein Polymer Films on Silicon Devices, Materials Research Society Synthesis and Thermoelectric Properties, 330:171-177 (1994).
Bai, J. et al., Regenerated spider silk as a new biomaterial for MEMS, Biomed Microdevices, 8:317-323 (2006).
Chrisey, D.B. et al., Laser Deposition of Polymer and Biomaterial Films, Chem. Rev 103(2):553-576 (2003).
Extended European Search Report for EP 09767706.6, 6 pages (dated Jan. 8, 2013).
Extended European Search Report for EP 13156510.3, 7 pages (dated Oct. 11, 2013).
Extended European Search Report for EP 13156523.6, 9 pages (dated Dec. 18, 2013).
Fukuoka T. et al., Enzymatic Polymerization of Tyrosine Derivatives. Peroxidase- and Protease-Catalyzed Synthesis of Poly(tyrosine)s with Different Structures, Biomacromolecules 3(4):768-774 (2002).
International Search Report for PCT/US2007/083600, 3 pages (dated Nov. 5, 2008).
International Search Report for PCT/US2007/083620, 3 pages (dated Dec. 5, 2008).
International Search Report for PCT/US2007/083634, 3 pages (dated Nov. 5, 2008).
International Search Report for PCT/US2007/083634, dated Nov. 5, 2008, 5 pages.
International Search Report for PCT/US2007/083642, 3 pages (dated Nov. 5, 2008).
International Search Report for PCT/US2007/083646, 4 pages (dated Dec. 15, 2008).
International Search Report for PCT/US2011/032195, 3 pages (dated Oct. 27, 2011).
International Search Report of PCT/US2007/083605, dated Dec. 15, 2008, 6 pages.
International Search Report of PCT/US2007/083639, dated Dec. 12, 2008, 5 pages.
International Search Report of PCT/US2008/082487, dated Feb. 27, 2009, 3 pages.
International Search Report of PCT/US2009/047751, dated Feb. 2, 2010, 3 pages.
International Search Report of PCT/US2010/022701, dated Mar. 31, 2010, 2 pages.
International Search Report of PCT/US2010/024004, dated Nov. 26, 2010, 5 pages.
International Search Report of PCT/US2010/042585, dated May 25, 2011, 8 pages.
International Search Report of PCT/US2010/047307, dated Apr. 28, 2011, 3 pages.
International Search Report of PCT/US2010/050468, dated Jan. 6, 2011, 3 pages.
International Search Report of PCT/US2011/028094, dated Jul. 14, 2011, 4 pages.
International Search Report of PCT/US2011/041002, 4 pages (dated Feb. 29, 2012).
IPRP for PCT/US2007/083642, 6 pages (May 5, 2009).
IPRP of PCT/US2007/083600, mailed May 5, 2009, 6 pages.
IPRP of PCT/US2007/083605, mailed May 5, 2009, 10 pages.
IPRP of PCT/US2007/083620, mailed May 5, 2009, 6 pages.
IPRP of PCT/US2007/083634, mailed May 5, 2009, 6 pages.
IPRP of PCT/US2007/083639, mailed May 5, 2009, 6 pages.
IPRP of PCT/US2007/083646, mailed May 5, 2009, 10 pages.
IPRP of PCT/US2008/082487, mailed May 11, 2010, 10 pages.
IPRP of PCT/US2009/047751, mailed Dec. 18, 2010, 5 pages.
IPRP of PCT/US2010/022701, mailed Aug. 2, 2011, 5 pages.
IPRP of PCT/US2010/024004, mailed Aug. 16, 2011, 6 pages.
IPRP of PCT/US2010/042585, mailed Jan. 24, 2012, 6 pages.
IPRP of PCT/US2010/047307, mailed Mar. 6, 2012, 5 pages.
Jiang, W. et al, Silicon and Polymer Nanophotonic Devices Based on Photonic Crystals, Proceedings of the International Society of Optical Engineering, 6124(1):612410-1(2006).
Jin, H.J. et al., Water-Stable Silk Films with Reduced β-Sheet Content, Advanced Functional Materials, 15:1241-1247 (2005).
Joglekar, A.P. et al., A study of the deterministic character of optical damage by femtosecond laser pulses and applications to nanomachining, Appl. Phys. B., 77: 25-30 (2003).
Kouba et al., Fabrication of Nanoimprint Stamps for Photonic Crystals, Journal of Physics: Conference Series, 34(1):897-903 (2006).
Lawrence, B.D. et al., Bioactive silk protein biomaterial systems for optical devices, Biomacromolecules, 9:1214-1220 (2008).

(56) References Cited

OTHER PUBLICATIONS

Liu, Y. et al., 3D femtosecond laser patterning of collagen for directed cell attachment, Biomaterials, 26(22):4597-605 (2005).
Min, B.M. et al., Regenerated Silk Fibroin Nanofibers: Water Vapor-Induced Structural Changes and Their Effects on the Behavior of Normal Human Cells, Macromol. Biosci., 6(4):285-292 (2006).
Minoura, N. et al., Attachment and Growth of Cultured Fibroblast Cells on Silk Protein Matrices, J. Biomed. Mater. Res. 29(10):1215-1221 (1995).
Notification of Transmittal of International Search Report and the Written Opinion of PCT/US2011/032195, dated Oct. 27, 2011, 2 pages.
Partial European Search Report for EP 13156523.6, 6 pages (dated Aug. 28, 2013).
Ramanujam, P.S., Optical Fabrication of Nano-Structured Biopolymer Surfaces, Opt. Mater. 27:1175-1177 (2005).
Tamada, Y., New Process to Form a Silk Fibroin Porous 3-D Structure, Biomacromolecules, 6:3100-3106 (2005).
Tu, D. et al., A ZEP520-LOR Bilayer Resist Lift-Off Process by E-Beam Lithography For Nanometer Pattern Transfer, Proceedings of the 7th IEEE Conference on Nanotechnology, 624-627 (2007).
Verma, M.K. et al., Embedded Template-Assisted Fabrication of Complex Microchannels in PDMS and Design of a Microfluidic Adhesive, Langmuir, 22(24)10291-10295 (2006).
Wang, L. et al., Fabrication of Polymer Photonic Crystal Superprism Structures Using Polydimethylsiloxane Soft Molds Journal of Applied Physics, 101(11):114316/1-6 (2007).
Wang, X. et al., Biomaterial coatings by stepwise deposition of silk fibroin, Langmuir, 21(24):11335-41 (2005).
Written Opinion for PCT/US2011/032195, 5 pages (dated Oct. 27, 2011).
Written Opinion for PCT/US2007/083600, 5 pages (dated Nov. 5, 2008).
Written Opinion for PCT/US2007/083620, 5 pages (dated Dec. 5, 2008).
Written Opinion for PCT/US2007/083634, dated Nov. 5, 2008 (5 pages).
Written Opinion for PCT/US2007/083642, 5 pages (dated Nov. 5, 2008).
Written Opinion for PCT/US2007/083646, 9 pages (dated Dec. 15, 2008).
Written Opinion of PCT/US2007/083605, dated Dec. 15, 2008, 9 pages.
Written Opinion of PCT/US2007/083639, dated Dec. 12, 2008, 5 pages.
Written Opinion of PCT/US2008/082487, dated Feb. 27, 2009, 9 pages.
Written Opinion of PCT/US2009/047751, dated Feb. 2, 2010, 4 pages.
Written Opinion of PCT/US2010/022701, dated Mar. 31, 2010, 4 pages.
Written Opinion of PCT/US2010/024004, dated Nov. 26, 2010, 5 pages.
Written Opinion of PCT/US2010/042585, dated May 25, 2011, 5 pages.
Written Opinion of PCT/US2010/047307, dated Apr. 28, 2011, 4 pages.
Xu, P. and Kaplan, D.L., Horseradish peroxidase catalyzed polymerization of tyrosine derivatives for nanoscale surface patterning, Journal of Macromolecular Science, Part A: Pure and Applied Chemistry, 41(12):1437-1445 (2004).
Yang, L.J. et al., Fabrication of SU-8 embedded microchannels with circular cross-section, International Journal of Machine Tools & Manufacturing, 44:1109-1114 (2004).
Whitesides, G. M. et al, Soft Lithography in Biology and Biochemistry, Annu. Rev. Biomed. Eng., 3:335-73 (2001).

\* cited by examiner

ELECTROACTIVE BIOPOLYMER OPTICAL AND ELECTRO-OPTICAL DEVICES AND METHOD OF MANUFACTURING THE SAME

CROSS-REFERENCE TO RELATED APPLICATIONS

This application is a Continuation of U.S. patent application Ser. No. 13/940,168, filed on Jul. 11, 2013, which is a Continuation of U.S. patent application Ser. No. 12/513, 392, filed on May 4, 2009, which is now U.S. Pat. No. 8,574,461, which is a National Stage Entry of PCT/US2007/ 083639, entitled "ELECTROACTIVE BIOPOLYMER OPTICAL AND ELECTRO-OPTICAL DEVICES AND METHOD OF MANUFACTURING THE SAME" filed Nov. 5, 2007, which claims the benefit of priority of U.S. Provisional Application Ser. No. 60/856,297 filed on Nov. 3, 2006, entitled "Biopolymer Devices and Methods for Manufacturing the Same."

GOVERNMENT SUPPORT

The invention was made with government support under grant number EB002520 awarded by the National Institutes of Health, DMR0402489 awarded by the National Science Foundation, and FA9550-04-1-0363 awarded by the United States Air Force. The government has certain rights in the invention.

BACKGROUND OF THE INVENTION

Field of the Invention

The present invention is directed to electroactive biopolymer optical and electro-optical devices and methods for manufacturing such devices. The present invention is further directed to electronics and electrical integration to biopolymer optical and electro-optical devices.

Description of Related Art

The field of optics is well established. Some subfields of optics include diffractive optics, micro-optics, photonics and guided wave optics. Various optical devices have been fabricated in these and other subfields of optics for research and commercial application. For example, common optical devices include diffraction gratings, photonic crystals, optofluidic devices, waveguides, lenses, microlens arrays, pattern generators, beam reshapers, and the like.

These optical devices are fabricated using various methods depending on the application and the optical characteristics desired. However, these optical devices, and the fabrication methods employed in their manufacture, generally involve significant use of non-biodegradable materials. For example, glass, fused silica, and plastic are commonly used in optical devices. Such materials are not biodegradable and remain in the environment for extended periods of time after the optical devices are removed from service and discarded. Of course, some of the materials can be recycled and reused. However, recycling also requires expenditures of natural resources and adds to the environmental costs associated with such materials.

Therefore, there exists an unfulfilled need for optical devices that minimize the negative impact to the environment. In addition, there exists an unfulfilled need for optical devices that provide additional functional features that are not provided by conventional optical devices.

SUMMARY OF THE INVENTION

In view of the foregoing, objects of the present invention are to provide various novel biopolymer optical devices and methods for manufacturing such optical devices that may be used in various applications.

One aspect of the present invention is to provide electroactive biopolymer optical and electro-optical devices.

Another aspect of the present invention is to provide a method for manufacturing such biopolymer optical devices.

One advantage of the present invention is in providing biopolymer optical devices that minimize the negative impact to the environment.

Another advantage of the present invention is in providing biopolymer optical devices that are biocompatible.

Yet another advantage of the present invention is in providing biopolymer optical devices that have additional functional features that are not provided by conventional optical devices.

In the above regard, inventors of the present invention recognized that biopolymers, and especially silk proteins, present novel structure and resulting functions. For example, from a materials science perspective, silks spun by spiders and silkworms represent the strongest and toughest natural fibers known and present various opportunities for functionalization, processing, and biocompatibility. Over five millennia of history accompany the journey of silk from a sought-after textile to a scientifically attractive fiber. As much as its features captivated people in the past, silk commands considerable attention in this day and age because of its strength, elasticity, and biochemical properties. The novel material features of silks have recently been extended due to insights into self-assembly and the role of water in assembly. These insights, in turn, have led to new processing methods to generate hydrogels, ultrathin films, thick films, conformal coatings, three-dimensional porous matrices, solid blocks, nanoscale diameter fibers, and large diameter fibers.

Silk-based materials achieve their impressive mechanical properties with natural physical crosslinks of thermodynamically stable protein secondary structures also known as beta sheets ($\beta$-sheets). As such, no exogenous crosslinking reactions or post process crosslinking is required to stabilize the materials. The presence of diverse amino acid side chain chemistries on silk protein chains facilitates coupling chemistry for functionalizing silks, such as with cytokines, morphogens, and cell binding domains. There are no known synthetic or biologically-derived polymer systems that offer this range of material properties or biological interfaces, when considering mechanical profiles, aqueous processing, room-temperature processing, ease of functionalization, diverse modes of processing, self-forming crosslinks, biocompatibility, and biodegradability.

Another unique feature provided by the biopolymer devices in accordance with the present invention, and especially the silk proteins, is the ability to genetically alter the native sequence of the biopolymer to add new functions, or to chemically modify the biopolymer to add new functions. The method and biopolymer devices of the present invention extend the capabilities of added cell binding domains (RGD), redox triggers (methionines for oxidation/reduction control), and phosphorylation triggers (enzymatic kinase/ phosphatase reactions). The biopolymer optical devices of the present invention further genetically redesign new versions of silk that retain native silk assembly and structure, but offer additional functions.

Additionally, using methods of the present invention, a variety of aromatic organic compounds, including tyrosines, can be enzymatically polymerized to generate conducting polymers. The polymerization of the organic compounds may be performed from solutions or in the solid state. This enzymatic process may be catalyzed by peroxidase enzyme reactions and is based on free radical coupling. The result is a carbon-carbon conjugated backbone that provides polymeric "wires" for use in polymer and biopolymer optical devices.

Further modifications to biopolymers such as silk may be made with tyrosines, either genetically or via chemical coupling. Tyrosines provide a molecular-level interface between the bulk silk protein and the optical features with a conducting layer or features via tyrosine-enzyme polymerization. Correspondingly, a unique, all-organic biopolymer electroactive material may be realized that also provides optical features.

More specifically, in accordance with the present invention, tyrosine monomers can be enzymatically crosslinked to form conducting polymers. The optical gratings made of biopolymers such as silk may be re-engineered to genetically encode tyrosine blocks in the silk. Tyrosine crosslinking may be used to form conducting wires, and further controls may be implemented to control the position at which the "wires" are formed, both internally and on the surface of the silk. As such, the present invention provides directed integration of electronic components into the biopolymer optical devices. These biopolymer materials, including silk, can be used for electronic properties for new conformal coatings and related technologies and include additional optical features.

The tyrosine moieties may be incorporated in the polymer or biopolymer such as silk via genetic engineering or via surface chemistry as a "functional" fusion component. For example, carbodiimide coupling may be used to incorporate the tyrosine moieties. Subsequent post processing polymerization via enzymatic processes generates conjugated conduits along the silk protein assemblies. The polymerization step is based on a secondary enzymatic polymerization with peroxidase to stitch the tyrosine carbon to carbon (C to C) bonds together to generate conducting polymers. The ability to form nanolayers, nanofibers, and related material systems with precise control of conducting polymer location and features provides new options for forming conformal, light weight, functional protective coatings with enhanced electronic and optical functions for a variety of applications.

Peroxidase catalysis, mediated by hydrogen peroxide, was used to form conducting polymers from a wide range of aromatic compounds. Horseradish peroxidase (HRP) is a glycoprotein that contains a single-chain β-type hemoprotein with an Fe containing porphyrin. HRP catalysis of aromatic compounds was used to form the conducting polymers. The solid-state polymerization reactions of aromatics on surfaces, via peroxidase catalyzed reactions, was used to form conducting polymers. In one embodiment of the present invention, dip-pen nanolithography (DPN) was used to pattern 4-aminothiophenol and tyrosines as the "ink". DPN patterning of an aromatic monomer, with surface induced orientation, was used to promote enzymatic polymerization under ambient surface reactions to form conducting polymers.

An example surface reaction may include a 0.01 M $H_2O_2$ stock solution, prepared by diluting $H_2O_2$ water solution (30% w/w) with $MeOH/H_2O$ (1:1 by volume) mixture. Peroxidase or hematin catalyzed polymerization may be carried out by immersing the solid state assemblies (either self-standing or on the surface of glass slides) into the $H_2O_2$ stock solution, which contains 200 μL horseradish peroxidase stock solution. The silk assembly is washed by dipping it in buffer solutions several times after the reaction. The peroxidase (donor: hydrogen peroxide oxidoreductase; EC 1.11.1.7, Type II, from horseradish, and hematin (procine) are commercially available.

Hematin provides benefits in the solid state material reactions due to the smaller size of the molecule compared to horseradish peroxidase, which relates to diffusion of the tyrosines not at the surface of the bulk materials, for example, with internal blocks. A typical hematin reaction includes sodium phosphate buffer, the silk material, and hematin. An equal molar amount of hydrogen peroxide (0.6 mmol) is added as oxidant, as in the peroxidase reactions.

Various applications exist for the electroactive biopolymer devices in accordance with the present invention. For example, the electroactive biopolymer devices may be used as electro-optical collectors, solar collectors, mechanical actuators with optical readout, and in other applications where light-weight, degradable, electroactive devices are desired.

While no other biopolymer or synthetic polymer can match the range of features outlined above for silk, the inventors of the present invention have identified some other polymers that exhibit various properties similar or analogous to silk. In particular, other natural biopolymers including chitosan, collagen, gelatin, agarose, chitin, polyhydroxyalkanoates, pullan, starch (amylase amylopectin), cellulose, hyaluronic acid, and related polymers have been identified. In view of the above-noted features of biopolymers and of silk in particular, the present invention provides novel biopolymer optical devices and methods for manufacturing such devices.

In accordance with one aspect of the present invention, a method of manufacturing a conducting polymer includes providing a polymer, providing a substrate, casting the polymer on the substrate, and enzymatically polymerizing an organic compound to generate a conducting polymer between the provided polymer and the substrate. In one embodiment, the polymer provided is a biopolymer, such as silk, while in other embodiments, other polymers may be used including chitosan, collagen, gelatin, agarose, chitin, polyhydroxyalkanoates, pullan, starch (amylose amylopectin), cellulose, hyaluronic acid, polydimethylsiloxane (PDMS), and related biopolymers, or variations and combinations thereof.

In one embodiment, the polymer may be a matrix solution, and the polymerization is performed from the matrix solution, while in other embodiments, the polymer may be a solid, and the polymerization is performed from the solid. Additionally, in one embodiment, the enzymatic polymerization may include catalyzing the organic compound with peroxidase enzyme reactions. For example, in one embodiment, tyrosine is used as the organic compound, while in other embodiments, other organic compounds may be used including red blood cells, horseradish peroxidase, phenolsulfonphthalein, nucleic acid, a dye, a cell, an antibody, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules (e.g., drugs, dyes, amino acids, vitamins, antioxidants), DNA, RNA, RNAi, lipids, nucleotides, aptamers, carbohydrates, chromophores, light emitting organic compounds such as luciferin, carotenes and light emitting inorganic compounds (such as chemical dyes), antibiotics, antifungals, antivirals, light harvesting compounds such as chlorophyll, bacteriorhodopsin, protorhodopsin, and porphyrins and related electronically active compounds, or variations and combinations thereof.

In one embodiment of the present invention, an interface is formed between the polymer and the substrate, where the interface is a conducting layer formed by tyrosine-enzyme polymerization. The interface may include a carbon to carbon (C to C) conjugated backbone.

In one embodiment, the substrate may act as a mold or a template for an optical device. The substrate may be a mold or template for electro-optical collectors, solar collectors, mechanical actuators with optical readout, and other applications where light-weight, degradable, electroactive devices are desired. The substrate may also be a mold of template for biopolymer devices including lenses, microlens arrays, optical gratings, pattern generators, beam reshapers, and the like. Other geometric features, such as holes and pits, for example, may also be included in the substrate.

In accordance with another embodiment of the present invention, a conducting polymer is provided that is made of at least a bulk protein, a substrate, an organic compound, and an enzyme that polymerizes the organic compound to generate a conducting polymer between the polymer and the substrate. The conducting polymer may be a biopolymer, such as silk, or may be another polymer including chitosan, collagen, gelatin, agarose, polyhydroxyalkanoates, pullan, starch (amylose amylopectin), cellulose, hyaluronic acid, polydimethylsiloxane (PDMS), and related biopolymers, or combinations thereof.

These and other advantages and features of the present invention will become more apparent from the following detailed description of the preferred embodiments of the present invention when viewed in conjunction with the accompanying drawings.

DETAILED DESCRIPTION OF THE INVENTION

In view of the superior functional characteristics and processability noted above, the biopolymer optical devices in accordance with the present invention are described as being fabricated using a biopolymer such as silk. In this regard, the silk utilized was silkworm silk. However, there are many different silks, including spider silk, transgenic silks, and genetically engineered silks, variants and combinations thereof and others, that may alternatively be used to manufacture biopolymer optical devices in accordance with the present invention.

In addition, other biodegradable polymers may be used instead of silk. For example, other biopolymers, such as chitosan, exhibit desirable mechanical properties, can be processed in water, and form generally clear films for optical applications. Other biopolymers, such as collagen, cellulose, chitin, hyaluronic acid, amylase, and the like may alternatively be utilized in specific applications. Synthetic biodegradable polymers such as polyactic acid, polyglycolic acid, polyhydroxyalkanoates, and related copolymers may also be selectively used. Such polymers may be used by themselves, or in combination with silk and other polymers and may be used to manufacture biopolymer optical devices for specific applications.

Figure 1A:
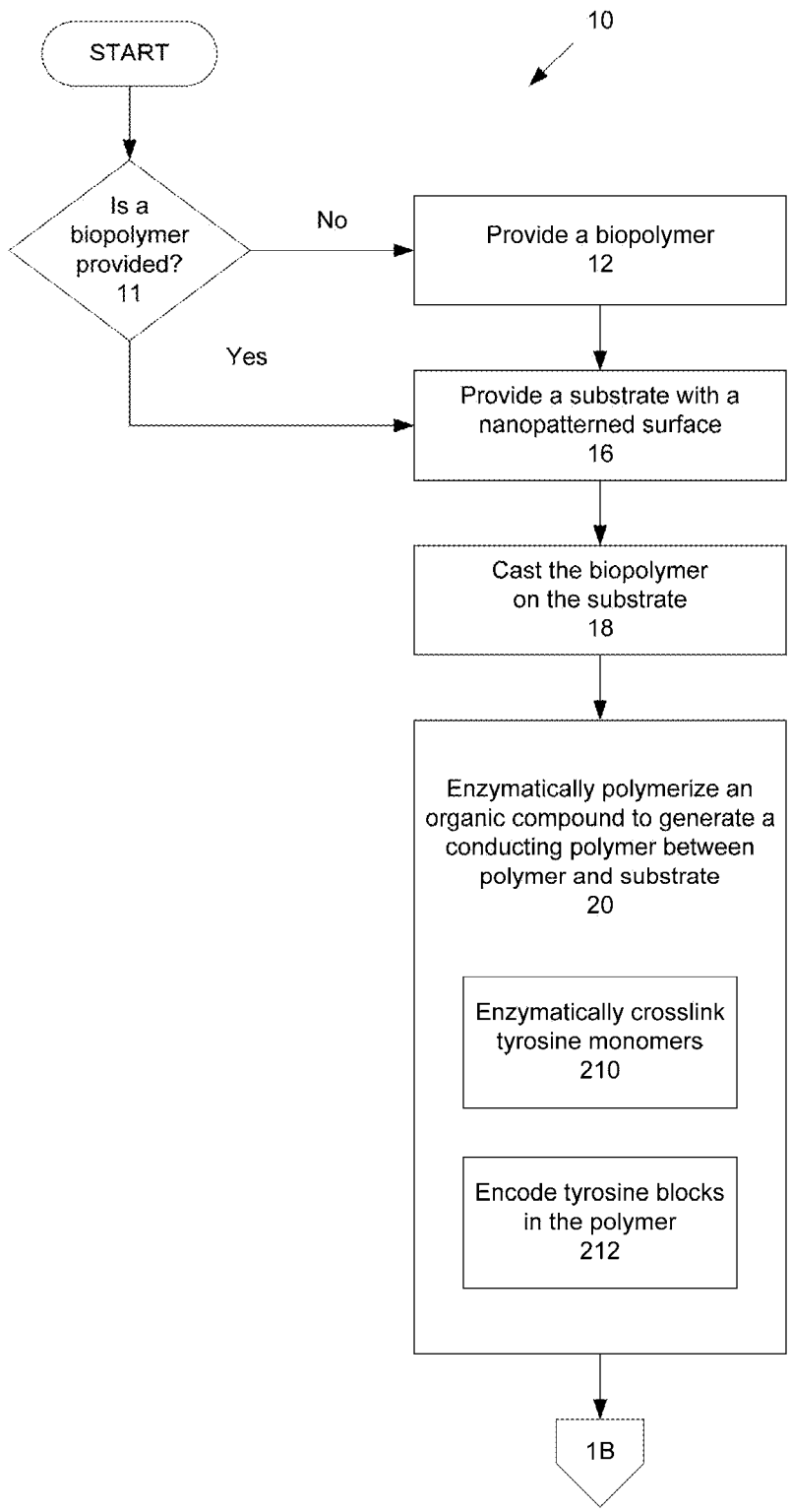
FIGS. 1A and 1B are schematic flow diagrams illustrating a method of manufacturing a biopolymer optical device in accordance with one embodiment of the present invention.

FIG. 1A is a schematic illustration of a flow diagram 10 showing a method of manufacturing a biopolymer optical device in accordance with one embodiment of the present invention. If a biopolymer is provided in step 11, the process proceeds to step 16 below. Otherwise, a biopolymer is provided in step 12. In the example where the biopolymer is silk, the biopolymer may be provided by extracting sericin from the cocoons of *Bombyx muni*. In one embodiment, the biopolymer may be a solution such as a biopolymer matrix solution, while in other embodiments, different solvents other than water, or a combination of water and other solvents may be used, depending on the biopolymer used.

In the example of silk, an aqueous silk fibroin solution may be processed, for example, 8.0 wt %, which is then used to manufacture the biopolymer optical device. Of course, in other embodiments, the solution concentrations may also be varied from very dilute (approximately 1 wt %) to very high (up to 30 wt %) using either dilution or concentration, for example, via osmotic stress or drying techniques. In this regard, other embodiments may utilize different percent weight solutions to optimize flexibility or strength of the resultant nanopatterned biopolymer optical device, depending on the application. Production of aqueous silk fibroin solution is described in detail in WIPO Publication Number WO 2005/012606 entitled "Concentrated Aqueous Silk Fibroin Solution and Uses Thereof," which is incorporated by reference. Additionally, the polymer may be a solid, and the polymerization is then performed using the solid.

A substrate is provided in step 16 to serve as a mold or template in manufacturing the biopolymer optical device. A surface of the substrate has the desired characteristic features to be formed on the biopolymer optical device. In this regard, the substrate may be an appropriate nanopattern on a surface of the optical device and may be an optical device such as a nanopatterned optical grating or other optical device, depending on the optical features desired for the device being manufactured. The polymer, such as the aqueous biopolymer matrix solution or the solid described above, is cast on the substrate in step 18. Upon drying, and upon completion of the subsequent reactions, a solidified biopolymer film is formed on the surface of the substrate. The thickness of the biopolymer film depends on the volume of the biopolymer matrix solution or the solid polymer applied to the substrate.

Patterned nanostructures can be provided on the biopolymer films, such as the silk films manufactured in the above discussed manner. In one embodiment, the surface of the substrate may be smooth so as to provide a smooth biopolymer film, and a nanopattern may be machined on the surface of the biopolymer film. The nanopattern may be machined using a laser, such as a femtosecond laser, or by other nanopattern machining techniques, including lithography techniques such as photolithography, electron beam lithography, and the like. Using such techniques, nanopattern features as small as 700 nm that are spaced less than 3 µm have been demonstrated as described in further detail below.

In another embodiment, the surface of the substrate itself may have an appropriate nanopattern thereon so that when the solidified biopolymer film is removed from the substrate, the biopolymer film is already formed with the desired nanopattern on a surface thereof. In such an implementation, the substrate may be an optical device such as a nanopatterned optical grating, depending on the nanopattern desired on the biopolymer films. The substrate surfaces may be coated with Teflon™ and other suitable coatings to ensure even detachment after the biopolymer matrix solution transitions from the liquid to the solid phase. The ability of the biopolymer casting method using a nanopatterned substrate for forming highly defined nanopatterned structures in the resultant biopolymer films was verified, and silk films having nanostructures as small as 75 nm and RMS surface roughness of less than 5 nm have been demonstrated.

Referring again to FIG. 1A, in step 20, an organic compound is enzymatically polymerized to generate a conducting polymer between the provided polymer and the substrate. The enzymatic reaction genetically alters the native sequence of the silk protein to add new functions or chemically modifies the biopolymer to add new functions, depending upon the polymer (for example, the silk protein) chosen and the enzyme reaction components. The method of the present invention extends the capabilities of added cell binding domains (Arginine-Glycine-Aspartic acid—RGD), redox triggers (methionines for oxidation/reduction control), and phosphorylation triggers (enzymatic kinase/phosphatase reactions). The enzymatic polymerization of the silk proteins of the present invention further genetically redesigns new versions of silk that retain native silk assembly and structure, but offer additional functions.

In one embodiment, the polymerized organic compound may be aromatic organic compounds such as amino acids, including tyrosines, that can be enzymatically polymerized to generate conducting polymers. As indicated above, the polymerization of the organic compounds may be performed from a solution or from a solid state.

Further modifications to biopolymers such as silk may be made with tyrosines, either genetically or via chemical coupling. Tyrosines provide a molecular-level interface between the bulk silk protein and the optical features with a conducting layer or with features via tyrosine-enzyme polymerization. Correspondingly, a unique, all-organic biopolymer electroactive material may be realized that also provides optical features.

More specifically, as shown in step 210, tyrosine monomers can be enzymatically crosslinked to form conducting polymers. The optical gratings made of biopolymers such as silk may be re-engineered to genetically encode tyrosine blocks in the silk as shown in step 212.

Figure 1B:
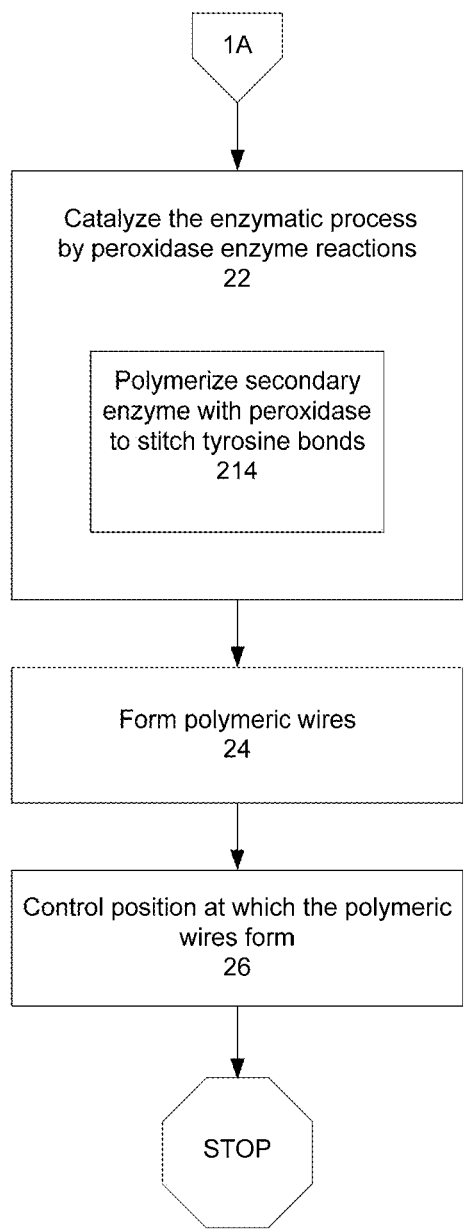

As shown in step 22 in FIG. 1B, the enzymatic process may be catalyzed by peroxidase enzyme reactions and is based on free radical coupling. For example, peroxidase catalysis, mediated by hydrogen peroxide, was used to form conducting polymers from a wide range of aromatic compounds. Horseradish peroxidase (HRP) is a glycoprotein that contains a single-chain β-type hemoprotein with an Fe containing porphyrin. HRP catalysis of aromatic compounds was used to form the conducting polymers. The solid-state polymerization reactions of aromatics on surfaces, via peroxidase catalyzed reactions, was used to form conducting polymers. In one embodiment of the present invention, dip-pen nanolithography (DPN) was used to pattern 4-aminothiophenol and tyrosines as the "ink". DPN patterning of an aromatic monomer, with surface induced orientation, was used to promote enzymatic polymerization under ambient surface reactions to form conducting polymers.

The tyrosine moieties can be incorporated in the biopolymer such as silk via genetic engineering or via surface chemistry as a "functional" fusion component. For example, carbodiimide coupling may be used to incorporate the tyrosine moieties. Subsequent post processing polymerization via enzymatic processes generates conjugated conduits along the silk protein assemblies. As shown in step 214, the polymerization step is based on a secondary enzymatic polymerization with peroxidase to stitch the tyrosine carbon to carbon (C to C) bonds together to generate conducting polymers. The ability to form nanolayers, nanofibers, and related material systems with precise control of conducting polymer location and features provides new options for forming conformal, light weight, functional protective coatings with enhanced electronic and optical functions for a variety of applications.

An example surface reaction may include a 0.01 M $H_2O_2$ stock solution, prepared by diluting $H_2O_2$ water solution (30% w/w) with $MeOH/H_2O$ (1:1 by volume) mixture. Peroxidase or hematin catalyzed polymerization can be carried out by immersing the solid state assemblies (either self-standing or on the surface of glass slides) into the $H_2O_2$ stock solution which contains 200 µL horseradish peroxidase stock solution. The silk assembly is washed by dipping it in buffer solutions several times after the reaction. The peroxidase (donor: hydrogen peroxide oxidoreductase; EC 1.11.1.7), Type II, from horseradish, and hematin (procine) are commercially available.

Hematin provides benefits in the solid state material reactions due to the smaller size of the molecule compared to horseradish peroxidase, which may relate to diffusion of the tyrosines not at the surface of the bulk materials, for example, with internal blocks. A typical hematin reaction includes sodium phosphate buffer, the silk material, and hematin. An equal molar amount of hydrogen peroxide (0.6 mmol) would be added as oxidant, as in the peroxidase reactions.

As shown in step 24, tyrosine crosslinking may be used to form conducting polymeric "wires" for the biopolymer optical device, resulting from a carbon-carbon (C to C) conjugated backbone. As shown in step 36, further controls may be implemented to control the position at which the "wires" are formed, both internally and on the surface of the silk. As such, directed integration of electronic components into the biopolymer optical devices may be performed in accordance with the present invention. These biopolymer materials, such as silk, can be used for electronic properties for new conformal coatings and related technologies and include additional optical features.

Various applications of the electroactive biopolymer devices include use as electro-optical collectors, solar gelatin, mechanical actuators with optical readout, and other applications where light-weight, degradable, electroactive devices can be used.

Figure 2:
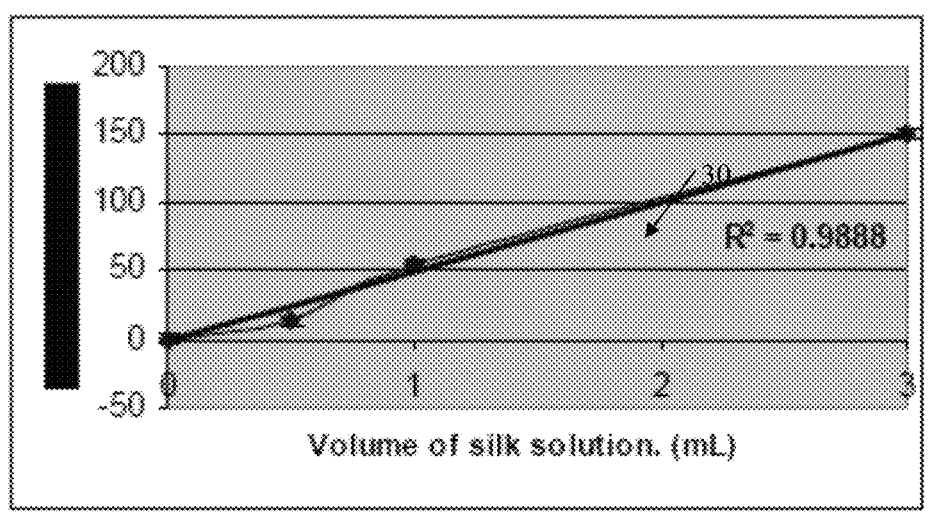
FIG. 2 is a graph that illustrates the relationship between the volume of 8% silk concentration vs. film thickness.

Experiments were conducted to validate the above-described method by manufacturing various biopolymer optical waveguides. The relationship between the volume of 8 wt % silk concentration aqueous silk fibroin solution, and the resulting silk film thickness, is shown in the graph 30 of FIG. 2, where the aqueous silk fibroin solution was cast over a substrate surface of approximately 10 square centimeters. The X-axis shows the volume of silk fibroin solution in mL, and the Y-axis shows the thickness of the resultant film in μm.

Of course, the film properties such as thickness and biopolymer content, as well as optical features, may be altered based on the concentration of fibroin used in the process, the volume of the aqueous silk fibroin solution or solid deposited, and the post-deposition process for drying the cast solution to lock in the structure. Accurate control of these parameters is desirable to ensure the optical quality of the resultant biopolymer optical waveguide and to maintain various characteristics of the biopolymer optical waveguide, such as transparency, structural rigidity, and flexibility. Furthermore, additives to the biopolymer matrix solution may be used to alter features of the biopolymer optical waveguide such as morphology, stability, and the like, as known with polyethylene glycols, collagens, and the like.

Figure 3A:
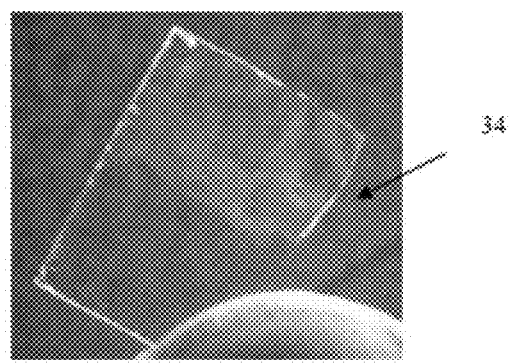
FIG. 3A is a photograph of a biopolymer film made of silk.
Figure 3B:
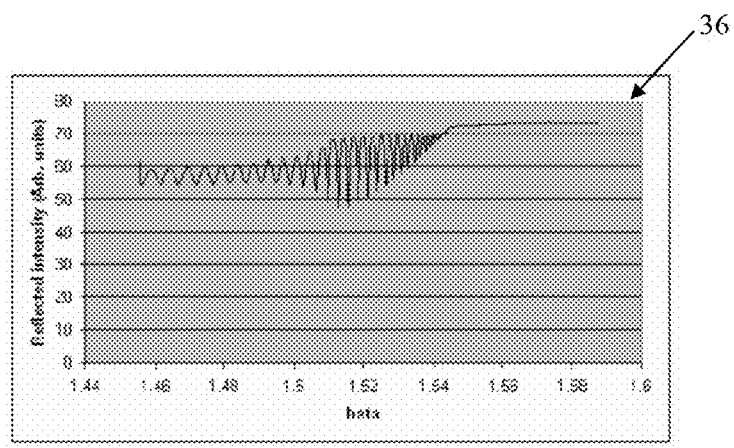
FIG. 3B is a graph showing the prism coupled angular dependence of reflectivity of the biopolymer film of FIG. 8A.

An unpatterned biopolymer film having a thickness of 10 μm was manufactured in the above-described manner using an aqueous silk fibroin solution, and was characterized in a scanning prism coupled reflectometer from Metricon Corporation. FIG. 3A illustrates the unpatterned biopolymer film 34 manufactured and characterized. The index of refraction of the biopolymer film 34 was measured to be n=1.55 at 633 nm, which is slightly higher than the index of refraction of conventional borosilicate glass. The measured index of refraction confirms that the value is high enough to afford reasonable contrast for optical use such as in air-silk biophotonic crystals (BPC) ($\Delta n_{fibroin} - \Delta n_{air} = 0.55$). The characterization of the unpatterned silk film 34 is shown in graph 36 of FIG. 3B, which clearly demonstrates the prism coupled angular dependence of the reflectivity. The oscillations in graph 36 are due to coupling into guided waves, demonstrating the use of silk as a waveguide material.

The measured roughness of cast silk film on an optically flat surface shows measured root mean squared roughness values between 2.5 and 5 nanometers, which implies a surface roughness easily less than λ/50 at a wavelength of 633 nm. Atomic force microscope images of patterned silk diffractive optics show the levels of microfabrication obtainable by casting and lifting silk films off of appropriate molds. The images show definition in the hundreds of nanometer range and the sharpness of the corners indicates the possibility of faithful patterning down to the tens of nanometers.

Figure 3C:
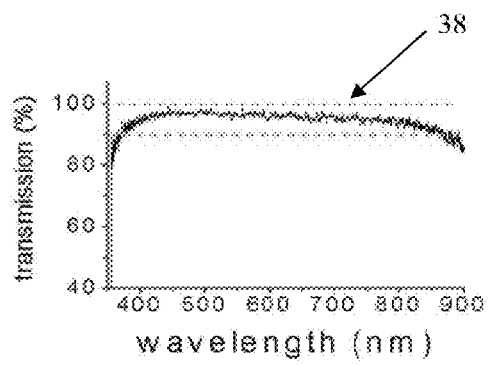
FIG. 3C is a graph showing the measured transmission of light through the biopolymer film of FIG. 8A.

In addition, the unpatterned silk film 34 was also analyzed to determine transparency. FIG. 3C is a graph 38 that illustrates the measured transmission of light through the silk film 34 in various wavelengths. Transmission measurements indicate that the unpatterned silk film 34 was highly transparent across the visible spectrum. For comparison, similar thickness films were also cast in collagen, and polydimethylsiloxane (PDMS). The free-standing structural stability was found to be inferior, and the resultant biopolymer optical device was not self-supporting when implemented as a thin film. However, such biopolymers may be used in other applications if structural stability is deemed to be not as important.

Importantly, shaped films having various thicknesses were patterned on the nanoscale using the method of FIG. 1 described above to provide nanopatterned biopolymer optical devices.

The term "nanopatterned" as used with regard to the present invention refers to very small patterning that is provided on a surface of the biopolymer optical device. The patterning has structural features whose size can be appropriately measured on a nanometer scale (that is, $10^{-9}$ meters), for example, sizes ranging from 100 nm to few microns. Additionally, the biopolymer optical devices of the present invention may incorporate various different optical devices such as lenses, diffraction gratings, photonic crystals, waveguides, and the like.

A variety of nanopatterned biopolymer optical devices were successfully manufactured using the above-described method of the present invention using silk fibroin solution. These devices included waveguides, lenses, microlens arrays, optical gratings, pattern generators, and beam reshapers. In particular, the aqueous solution of silk fibroin was cast onto specific substrates with patterns thereon. The substrate surfaces were coated with Teflon™ to ensure even detachment after the biopolymer matrix solution transitions from the liquid to the solid phase. The ability of the biopolymer casting method of the present invention for forming highly defined nanopatterned structures in biopolymer optical devices was verified by casting the optical waveguides of the present invention. Regular patterned features with dimensions down to 210 nm, and localized surface roughness of less than 20 nm, have been attained. As mentioned above, smoothing techniques may also be used to further reduce or remove surface roughness of the biopolymer optical waveguide.

Such regular patterning of biocompatible materials allows manufacturing of optical devices that can be used to provide photonic bandgaps and manipulate light via an organic, yet mechanically robust optical device. These devices combine the flexibility of embedded optics with the unique versatility of the protein substrate as explained throughout the application. Many advantages are provided by the present invention including combining the organic nature of biopolymers such as silk with the power of diffractive and transmissive optics embedded in an organic matrix to create biologically active optical elements. Silk provides a controllably degradable, biocompatible, and structurally strong medium with which to fabricate the optical devices in accordance with the present invention.

Transmissive nanopatterned diffractive biopolymer optical devices were made using the method of the present invention described above. These optical devices include biopolymer optical waveguides, silk diffusers, line pattern generators, and cross pattern generators. Such optical devices use appropriately configured wavelength scale surface structuring to create predefined one or two-dimensional light patterns that exploit light interference. Such optical devices made of conventional materials have been applied to imaging, spectroscopy, beam sampling and transformation, and metrology to name a few uses. Extending this approach to control the delivery of light within a biological matrix such as silk biopolymer can provide optimal coupling of photons into a substrate or allow for designed optical discrimination, interface, or readout.

A significant advantage of biopolymer optical waveguides in accordance with the present invention is the ability of the optical waveguides to be biologically activated since they are entirely organic and biocompatible. Water-based processing can be used, for example, for silk optical waveguides. This increases cellular survivability of the waveguides and the likelihood of biocompatibility.

To confirm biocompatibility of nanopatterned biopolymer optical devices, red blood cells (RBCs) were incorporated into a silk diffraction grating in accordance with the present invention that was manufactured as described above with regard to FIG. 1. The RBC-silk fibroin solution was prepared by combining 1 ml of an 80% hematocrit human RBC solution and 5 ml of the 8% silk solution. The mixture was cast on a 600 lines/mm optical grating and allowed to dry overnight. The film was removed from the optical grating and annealed for two hours. The grating structure was observed in the resultant RBC-doped silk diffraction grating.

Figure 4:
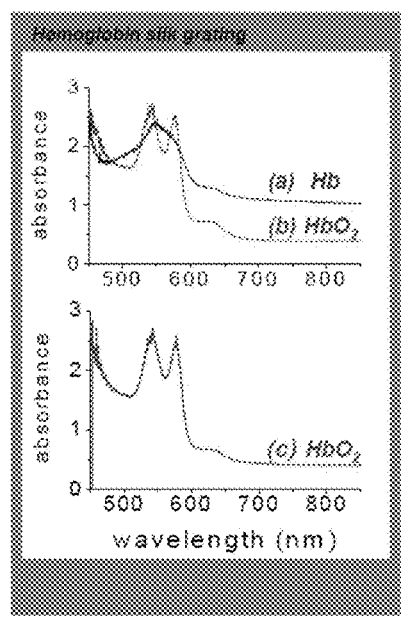
FIG. 4 illustrates results graphs showing retention of the hemoglobin function within an RBC-doped silk optical device.

The RBC-doped silk diffraction grating was then tested to observe the diffraction orders. An optical transmission experiment was performed to determine whether hemoglobin (the oxygen-carrying protein contained in RBCs) maintained its activity within the matrix of the silk diffraction grating. The results graphs 160 are shown in FIG. 4 and indicate the retention of hemoglobin function within the RBC-doped silk diffraction grating. The X-axis corresponds to the wavelength (in nm), and the Y-axis indicates the absorbance by the RBC-doped silk diffraction grating.

In particular, the RBC-doped silk diffraction grating was inserted in a quartz cuvette filled with distilled water, and an absorbance curve was observed. This result is shown by line (b) $HbO_2$ in results graphs 160. As can be seen, the absorbance curve shown by line (b) $HbO_2$ exhibited two peaks typical of oxy-hemoglobin absorption. Subsequently, nitrogen gas was bubbled into the cuvette to deoxygenate the hemoglobin. After 15 minutes, the characteristic absorption peaks of oxy-hemoglobin disappeared from the absorbance curve. This result is shown by line (a) Hb in the results graphs 160. These results were further confirmed when the nitrogen flow to the cuvette is subsequently halted, which resulted in the reappearance of the oxy-hemoglobin peaks. This result is shown by line (c) $HbO_2$ in results graphs 160.

Figure 5:
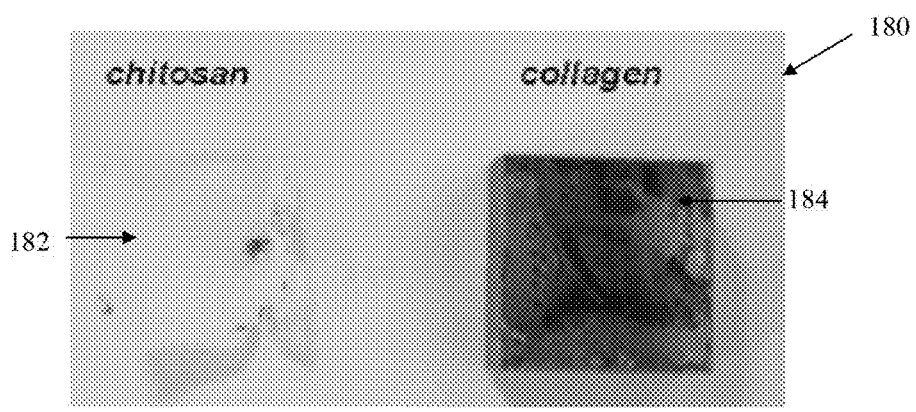
FIG. 5 is a photograph showing diffractive biopolymer devices that have been cast in silk, chitosan, and collagen.

As previously noted, alternative biopolymers may also be used for fabrication of nanopatterned biopolymer optical devices in accordance with the present invention. FIG. 5 shows a photograph 180 that illustrates other diffractive biopolymer optical devices that have been cast using different materials. In particular, a chitosan optical device 182 and a collagen optical device 184 have also been manufactured in accordance with the present invention. With respect to chitosan, optical diffraction characteristics similar to silk have been observed.

It should be evident from the above discussion and the example nanopatterned biopolymer optical devices shown and discussed that the present invention provides biodegradable biopolymer optical devices. High quality biopolymer optical devices were manufactured that are naturally biocompatible, can be processed in water, and can undergo degradation with controlled lifetimes. As explained above, the biopolymer optical devices of the present invention may also be biologically activated by incorporating small organic materials. In particular, the biopolymer optical devices can be biologically functionalized by optionally embedding it with one or more organic indicators, living cells, organisms, markers, proteins, and the like. More specifically, the biopolymer optical devices in accordance with the present invention may be embedded or coated with organic materials such as red blood cells, horseradish peroxidase, phenolsulfonphthalein, nucleic acid, a dye, a cell, an antibody, as described further in Appendix I, enzymes, for example, peroxidase, lipase, amylose, organophosphate dehydrogenase, ligases, restriction endonucleases, ribonucleases, DNA polymerases, glucose oxidase, laccase, cells, viruses, proteins, peptides, small molecules (e.g., drugs, dyes, amino acids, vitamins, antioxidants), DNA, RNA, RNAi, lipids, nucleotides, aptamers, carbohydrates, chromophores, light emitting organic compounds such as luciferin, carotenes and light emitting inorganic compounds (such as chemical dyes), antibiotics, antifungals, antivirals, light harvesting compounds such as chlorophyll, bacteriorhodopsin, protorhodopsin, and porphyrins and related electronically active compounds, tissues or other living materials, other compounds or combinations thereof. The embedded organic materials are biologically active, thereby adding biological functionality to the resultant biopolymer optical device.

The embedding of the biopolymer optical devices with organic materials may be performed for example, by adding such materials to the biopolymer matrix solution used to manufacture the biopolymer films, such as the silk fibroin matrix solution. In the implementation where the biopolymer optical device is manufactured using a solid, the optical device can be biologically functionalized by functionalizing of one or more of the polymer films.

The present invention broadens the versatility of optical devices by allowing the direct incorporation of labile biological receptors in the form of peptides, enzymes, cells, antibodies, or related systems, and the like and allows such optical devices to function as biological sensing devices.

The biopolymer optical devices of the present invention can be readily used in environmental and life sciences where biocompatibility and biodegradability are paramount. For example, the nanopatterned biopolymer optical devices as described above can be unobtrusively used to monitor a natural environment such as in the human body and may be implanted in vivo without a need to retrieve the device at a later time. The degradation lifetime of the biopolymer optical devices of the present invention can be controlled during the manufacturing process, for example, by controlling the ratio and amount of the solution matrix cast or the type of polymer used. Moreover, the biopolymer optical devices of the present invention can be dispersed in the environment, again without the need to retrieve them at a later time, thereby providing novel and useful devices for sensing and detection.

The foregoing description of the aspects and embodiments of the present invention provides illustration and description, but is not intended to be exhaustive or to limit the invention to the precise form disclosed. Those of skill in the art will recognize certain modifications, permutations, additions, and combinations of those embodiments are possible in light of the above teachings or may be acquired from practice of the invention. Therefore the present invention also covers various modifications and equivalent arrangements that fall within the purview of the appended claims.

Antibody Stability in Silk Films

Materials—Anti-IL-8 monoclonal antibody (IgG1) was purchased from eBioscience, Inc. human polyclonal antibody IgG and human IgG ELISA Quantitation Kit were purchased from Bethyl Laboratories Inc. All other chemicals used in the study were purchased from Sigma-Aldrich (St. Louis, Mo.).

Figure 6:
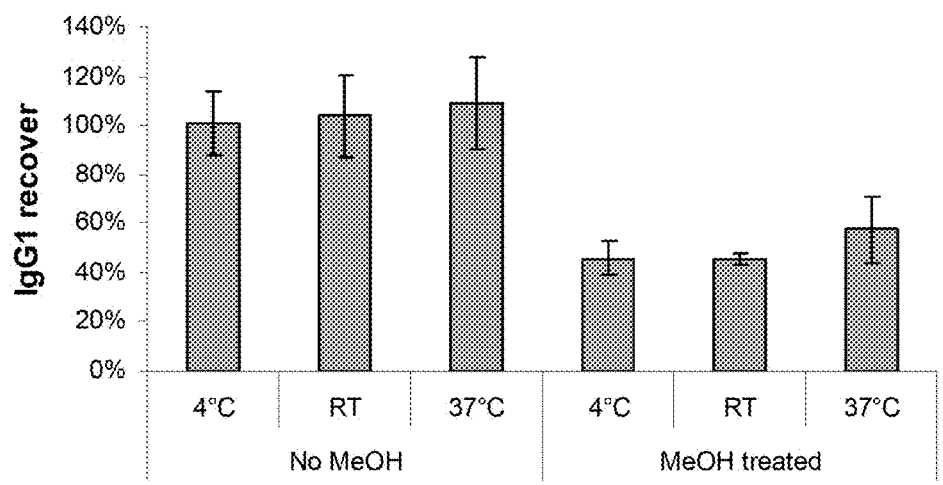
FIG. 6 is a graph showing antibody IgG1 activity related to initial activity in the silk films prepared in the two different formats and stored at the three different temperatures.

Antibody entrapment in silk films—human polyclonal antibody IgG—Ten ml 1 mg/ml IgG mixed with 167 ml 6% silk solution make the IgG concentration in silk film mg/g silk. 100 μl of mixed IgG solution was added to each well of 96 well plate which was placed in a fume hood with cover opened overnight. The dried film was either treated or not treated with methanol. For methanol treatment, the wells were immersed in 90% methanol solution for 5 min and dried in the fume hood. All dry 96 well plates were then stored at 4° C., room temperature, and 37° C. (FIG. 6).

Figure 7:
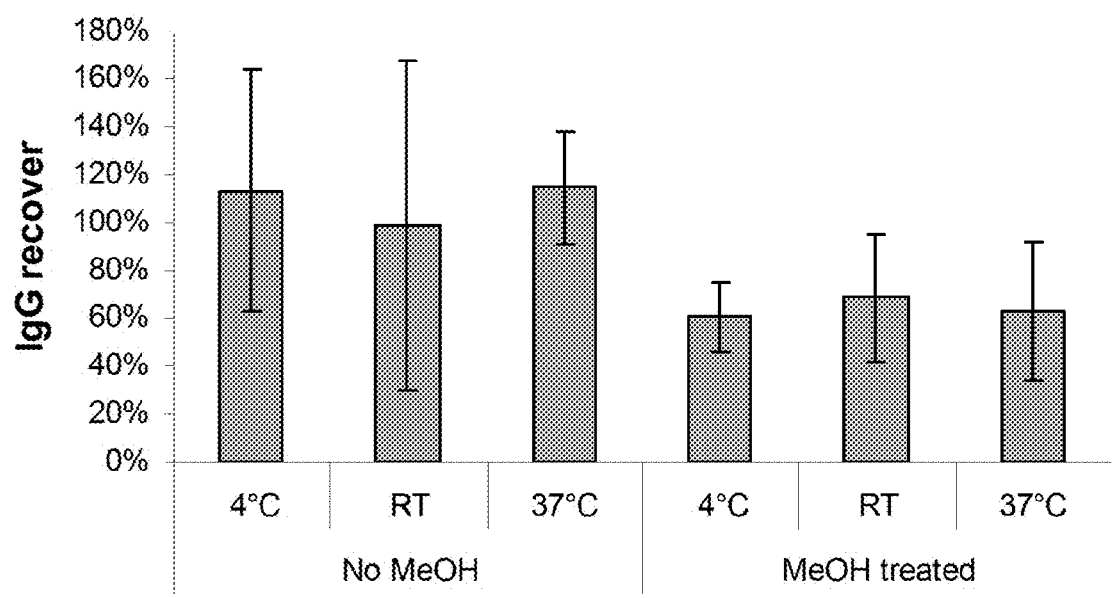
FIG. 7 is a graph showing antibody IgG activity related to initial activity in the silk films prepared in the two different formats and stored at the three different temperatures.

Anti-IL-8 monoclonal antibody (IgG1)—0.5 ml 1 mg/ml IgG1 mixed with 83 ml 6% silk solution make the IgG1 concentration in silk film 0.1 mg/g silk. 50 µl of mixed IgG1 solution was added to a well of 96 well plate which was placed in a fume hood with cover opened overnight. The dried film was either treated or not treated with methanol. For methanol treatment, the wells were immersed in 90% methanol solution for 5 min and dried in the fume hood. All dry 96 well plates were then stored at 4° C., room temperature, and 37° C. (FIG. 7).

Antibody measurement—Five wells prepared at the same condition were measured for statistic. Pure silk (without antibody) was used as a control.

For non methanol-treated samples, 100 µl of PBS buffer, pH 7.4, was added to the well which was further incubated at room temperature for 30 min to allow the film to completely dissolve. Aliquot of solution was then subjected to antibody measurement. For methanol-treated samples, 100 µl HFIP was added into each well which was further incubated at room temperature for 2 hours to allow the film completely dissolve. The silk HFIP solution was dried in a fume hood overnight. The follow step was the same as non methanol-treated samples, added PBS buffer and pipette the solution for antibody measurement.

ELISA—Polystyrene (96-well) microtitre plate was coated with 100 µL of antigen anti-Human IgG-affinity at a concentration of 10 µg/mL prepared in antigen coating buffer (bicarbonate buffer, 50 mM, pH 9.6) and then incubated overnight storage at room temperature. The wells were then washed three times with TBS-T buffer. The unoccupied sites were blocked with 1% BSA in TBS (200 µL each well) followed by incubation for 30 minutes at room temperature. The wells were then washed three times with TBS-T. The test and control wells were then diluted with 100 µL of serially diluted serum. Each dilution was in TBS buffer. Serially diluted blanks corresponding to each dilution were also present. The plate was then incubated for 1 h at room temperature. The plate was washed again with TBS-T buffer (five times). Bound antibodies were assayed with an appropriate conjugate of anti-human IgG-HRP (1:100,000), 100 µL of it was coated in each well and kept at room temperature for 1 hour. Washing of the plate with TBS-T (five times) was followed by addition of 100 µL TMB in each well and incubation at room temperature for 5-20 min. The absorbance of each well was monitored at 450 nm on a VersaMax microplate reader (Molecular devices, Sunnyvale, Calif.).

The claimed invention is:

1. An electroactive biopolymer optical device, comprising:
    a silk fibroin assembly, comprising:
        silk fibroin characterized by beta-sheet secondary structure, wherein the silk fibroin is genetically altered or chemically modified, wherein the silk fibroin comprises at least one tyrosine block;
        at least one polymeric wire, comprising crosslinked aromatic organic compounds coupled with the silk fibroin and characterized in that they are conducting, wherein the crosslinked aromatic organic compounds are arranged such that form a conducting backbone of the least one polymeric wire;
        wherein the at least one polymeric wire is formed internally within the silk fibroin assembly and/or on a surface of the silk fibroin assembly; and
    at least one shaped optical feature,
        wherein the at least one shaped optical feature is formed on the surface of the silk fibroin assembly and/or the at least one shaped optical feature is or forms a shape of the silk fibroin assembly.

2. The device of claim 1, wherein the silk fibroin comprises tyrosine monomers and the crosslinked aromatic organic compounds comprise tyrosine crosslinking.

3. The device of claim 2, wherein the tyrosine crosslinking comprises carbon-carbon bonds that form a conducting conjugated backbone.

4. The device of claim 2, wherein the tyrosine crosslinks form conjugated conduits along the surface and/or internally within the silk fibroin assembly.

5. The device of claim 1, wherein the crosslinks form internal conductive wires or conductive wires on a surface of the biopolymer.

6. The device of claim 1, wherein the at least one shaped optical feature is a patterned structure.

7. The device of claim 6, wherein the patterned structure is a nanopatterned structure.

8. The device of claim 1, wherein the device is selected from the group consisting of an electro-optical collector, a solar collector, a mechanical actuator with optical readout, a conformal coating, and a functionally protective coating.

9. The device of claim 1, wherein the at least one shaped optical feature is a diffractive or refractive structure selected from the group consisting of a beam diffuser, a diffraction grating, a photonic crystal, an optofluidic, a waveguide, a lens, a microlens array, a nanolens array, a pattern generator, and a beam reshaper.

10. The device of claim 1, wherein the silk fibroin assembly is a nanolayer, a nanofiber, or a film.

11. The device of claims 1, further comprising one or more small organic molecules.

12. The device of claims 1, further comprising organic indicators, cells, organisms, markers, or proteins.

13. The device of claims 1, further comprising red blood cells, horseradish peroxidase, phenolsulfonphthalein, nucleic acids, a dye, a cell, an antibody, enzymes, restriction endonucleases, ribonucleases, DNA polymerases, glucose oxidase, laccase, tissues, cells, antibodies, viruses, proteins, peptides, small molecules, drugs, dyes, amino acids, vitamins, antioxidants, DNA, RNA, RNAi, lipids, nucleotides, aptamers, carbohydrates, chromophores, light emitting organic compounds, luciferin, carotenes, light emitting inorganic compounds, antibiotics, antifungals, antivirals, light harvesting compounds, chlorophyll, bacteriorhodopsin, protorhodopsin, porphyrins, or electronically active compounds.

14. The device of claim 1, further comprising a substrate.

15. The device of claims 14, wherein the polymeric wires formed on the surface of the silk fibroin between the substrate and silk fibroin.

* * * * *